US005856523A

United States Patent [19]
Miao et al.

[11] Patent Number: 5,856,523
[45] Date of Patent: Jan. 5, 1999

[54] PURIFYING CYCLIC ESTERS BY AQUEOUS SOLVENT EXTRACTION AND FURTHER PURIFICATION

[75] Inventors: Fudu Miao, Louisville; Timothy J. Eggeman, Lakewood, both of Colo.

[73] Assignee: Chronopol, Inc., Golden, Colo.

[21] Appl. No.: 940,592

[22] Filed: Sep. 30, 1997

Related U.S. Application Data

[60] Division of Ser. No. 473,400, Jun. 6, 1995, Pat. No. 5,686,630, which is a continuation-in-part of Ser. No. 417,597, Apr. 5, 1995, Pat. No. 5,675,021, which is a continuation-in-part of Ser. No. 128,797, Sep. 29, 1993, Pat. No. 5,420,304, which is a continuation-in-part of Ser. No. 854,559, Mar. 19, 1992, Pat. No. 5,319,107.

[51] Int. Cl.$^6$ .................. C07D 319/00; C07D 319/12
[52] U.S. Cl. ................. 549/274; 549/263; 549/379
[58] Field of Search ................... 549/263, 274, 549/379

[56] References Cited

U.S. PATENT DOCUMENTS

| | | | |
|---|---|---|---|
| 1,095,205 | 5/1914 | Gruter et al. . | |
| 1,594,843 | 8/1926 | Lawrie . | |
| 1,906,068 | 4/1933 | Jenemann . | |
| 1,995,970 | 3/1935 | Dorough | 260/2 |
| 2,163,268 | 6/1939 | Carothers et al. | 260/338 |
| 2,174,491 | 9/1939 | Watson | 260/67 |
| 2,189,572 | 2/1940 | Watson | 260/78 |
| 2,668,162 | 2/1954 | Lowe | 260/78.3 |
| 2,703,316 | 3/1955 | Schneider | 260/78.3 |
| 2,758,987 | 8/1956 | Salzberg | 260/78.3 |
| 2,768,973 | 10/1956 | Castle et al. | 260/602 |
| 3,322,719 | 5/1967 | Peilstöcker | 260/45.8 |
| 3,322,791 | 5/1967 | Selman | 260/340.2 |
| 3,371,112 | 2/1968 | Winstrom et al. | 260/535 |
| 3,435,008 | 3/1969 | Schmitt et al. | 260/78.3 |
| 3,457,280 | 7/1969 | Schmitt et al. | 260/340.2 |
| 3,597,450 | 8/1971 | Schmitt et al. | 260/340.2 |
| 3,736,646 | 6/1973 | Schmitt et al. | 29/458 |
| 3,867,190 | 2/1975 | Schmitt et al. | 117/138.8 |
| 3,960,152 | 6/1976 | Augurt et al. | 128/335.5 |
| 4,033,938 | 7/1977 | Augurt et al. | 260/78.3 |
| 4,045,418 | 8/1977 | Sinclair | 260/78.3 |
| 4,070,375 | 1/1978 | Suzuki | 260/340.6 |
| 4,435,595 | 3/1984 | Agreda et al. | 560/234 |
| 4,650,851 | 3/1987 | Rhum et al. | 528/354 |
| 4,727,163 | 2/1988 | Bellis | 549/274 |
| 4,730,082 | 3/1988 | Amiet | 560/227 |
| 4,771,001 | 9/1988 | Bailey et al. | 435/139 |
| 4,797,468 | 1/1989 | DeVries | 549/274 |
| 4,835,293 | 5/1989 | Bhatia | 549/274 |
| 4,939,294 | 7/1990 | Agreda et al. | 560/265 |
| 4,966,982 | 10/1990 | Ono et al. | 549/274 |
| 4,990,222 | 2/1991 | Aigner et al. | 203/91 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,068,418 | 11/1991 | Kulprathipanja et al. | 562/580 |
| 5,075,115 | 12/1991 | Brine | 424/486 |
| 5,089,632 | 2/1992 | Paul | 549/274 |
| 5,091,544 | 2/1992 | Bhatia | 549/274 |
| 5,136,057 | 8/1992 | Bhatia | 549/274 |
| 5,236,560 | 8/1993 | Drysdale | 203/99 |
| 5,264,592 | 11/1993 | Fridman et al. | 549/274 |
| 5,274,127 | 12/1993 | Sinclair et al. | 549/274 |
| 5,310,599 | 5/1994 | Ford | 528/354 |
| 5,319,107 | 6/1994 | Benecke et al. | 549/274 |

FOREIGN PATENT DOCUMENTS

| | | | |
|---|---|---|---|
| 863673 | 2/1971 | Canada . | |
| 0 261 572 A1 | 3/1988 | European Pat. Off. . | |
| 0 264 926 A2 | 4/1988 | European Pat. Off. . | |
| 0 275 581 A1 | 7/1988 | European Pat. Off. . | |
| 53 074 | 5/1967 | German Dem. Rep. . | |
| 221786 | 5/1910 | Germany . | |
| 267826 | 12/1913 | Germany . | |
| DE 36 32 103 A1 | 3/1988 | Germany . | |
| 1007347 | 10/1965 | United Kingdom . | |
| 1122229 | 7/1968 | United Kingdom . | |
| WO 91/17155 | 11/1991 | WIPO . | |
| WO 92/00292 | 1/1992 | WIPO . | |
| WO 93/02075 | 2/1993 | WIPO | 549/274 |
| WO 93/15069 | 8/1993 | WIPO | 549/274 |

OTHER PUBLICATIONS

Alen et al., "Condensation Of Clycolic, Lactic and 2–Hydroxybutanoic Acids During Heating and Identification of the Condensation Products By GLC–MS", pp. 633–636, 1980 Acta Chemica Scandinavica B, vol. 34, No. 9.

Bezzi, "The Constitution of Some Polyglycolides", pp. 219–233, 1949, Gazz Chim. Ital. vol. 79.

Bezzi, "Transformation of Cyclic Esters Into Linear Polyesters", pp. 215–224, 1938, Gazz. Chim. Ital. vol. 68.

Bezzi et al., "Dehydration Products of Lactic Acid Typifying the Transformation of Cyclic Esters Into Linear Polyesters", 1936, Meeting of the Italian Academy of Science, Nov.

Bischoff et al., "Ueber Das Glycolid Und Seine Homologen", 1893, pp. 262–265, Chem. Ber, vol. 26.

Bureau, "What the Printer Should Know About Paper", pp. 38, 39, 59, Graphic Arts Technical Foundation.

Bosche, "Recovering Chemical Products From Dilute Fermentation Broths", pp. 597–615, 1983, Biotechnology And Bioengineering Symp., No. 13.

(List continued on next page.)

*Primary Examiner*—Robert E. Sellers
*Attorney, Agent, or Firm*—Sheridan Ross P.C.

[57] ABSTRACT

A process is provided for the production and purification of cyclic esters in which the purification includes the introduction of an aqueous solvent into a cyclic ester containing composition and allowing two phases to form. A first phase includes cyclic esters and any organic solvent, and a second phase includes the aqueous solvent and impurities.

16 Claims, 2 Drawing Sheets

OTHER PUBLICATIONS

Carothers et al., "Studies Of Polymerization And Ring Formation. X. The Reversible Polymerization Of Six–Membered Cyclic Esters", pp. 761–771, 1932, J. Am. Chem. Soc., vol. 54.

Carothers, "Polymers And Polyfunctionality", pp. 39–53, 1936, Transactions Of The Faraday Society, vol. 32.

Cleary et al., "Separation Of Closely Boiling Mixtures By Reactive Distillation. 2. Experiments", pp. 1071–1073, 1985, Ind. Eng. Chem. Proces Des. Dev., vol. 24.

Dadgar et al., "Improving The Acetone–Butanol Fermentation Process With Liquid–Liquid Extraction", pp. 36–39, 1988, Biotechnology Progress, vol. 4, No. 1.

DeGarmo et al., "Consider Reactive Distillation", pp. 43–50, 1992, Chemical Engioneering Progress, Mar.

Deibig et al., "I. Synthesis And Properties Of Polytetramethyl Glycolide", pp. 123–131, 1971, Die Makromolekulare Chemie, vol. 145.

Deibig et al., "II. Thermal Behavior Of Polytetramethyl Glycolide", pp. 133–139, 1971, Die Makromolekulare Chemie, vol. 145.

Earhart et al., Waste Recovery: Recovery Of Organic Pollutants Via Solvent Extraction, pp. 67–73, 1977, Cep, May.

Filachione et al., "Lactic Acid Condensation Polymers: Preparation By Batch And Continuous Methods", pp. 223–228, 1944, Industrial And Engineering Chemistry, Mar. vol. 36, No. 3.

Hill et al., "Cyclic And Polymeric Formals", pp. 925–928, 1935, J. Am. Chem. Soc., vol. 57.

Holten, "Lactic Acid. Properties And Chemistry Of Lactic Acid And Derivatives", pp. 221–231, 1971, Verlag Chemie.

Imasaka et al., "Synthesis Of Degradable Terpolymers Responding To External Stimuli Such As PH, Ionic Strength, And Temperature", pp. 715–722, 1991, Makromol. Chem. vol. 192.

Ikada et al., "Stereocomplex Formation Between Enantiomeric Poly(Lactides)", pp. 904–906, 1987, American Chemical Society, Macromolecules, 20.

Jackanicz et al., "Polylactic Acid As A Biodegradable Carrier For Contraceptive Steroids", pp. 227–234, 1973, The Population Counsel, Sep., vol. 8, No. 3.

Jungfleisch et al., "Organic Chemistry—of Lactyllactyllactic Acid and the Dilactide Of Racemic Lactic Acid", pp. 502–505, 1905, Academie Des Sciences, Meeting Of 20 Feb.

Jungfleisch et al., "Organic Chemistry—on the Dilactide of the Right", pp. 111–113, 1905 Academie Des Sciences, Meeting of 10 Jul.

Jungfleisch et al., "Organic Chemistry—on the Dilactide of Left Lactic Acid", pp. 637–639, 1906, Academie Des Sciences, Meeting Of 12 Mar.

Jungfleisch et al., "Organic Chemistry—on Ethyl Lactyllactate", 1907, Academie Des Sciences, Meeting Of 25 Feb.

Jungfleisch et al., "Organic Chemistry—on Inactive Dilactylic Acid", p. 979, 1907, Academie Des Sciences, Meeting of 6 May.

King, "Amine–Based Systems For Carboxylic Acid Recovery", pp. 285–291, 1992, Chemtech, Mar.

Kleine et al., "High Molecular Weight, Especially Optically Active Polyesters Of Lactic Acid: An Investigation of the Stereochemistry of Macromolecular Compounds", pp. 1–21, 1958, Report From the Research Laboratory for Macromolecular Chemistry, Dec.

Kulkarni et al., "Polylactic Acid for Surgical Implants", pp. 839–843, 1966, Arch. Surg., vol. 93, Nov.

Light, "Lactic Acid Resins", pp. 135–136, 1940, Paint Manufacture, Jun.

Marlatt et al., "Acetone–butanol Fermentation Process Development And Economic Evaluation", pp. 23–28, 1986, Biotechnology Progress, vol. 2, No. 1.

Montgomery, "Acidic Constituents of Lactic Acid–Water Systems", pp. 1466–1468, 1952, J. Am. Chem. Soc., vol. 74.

Othmer, "Acetic Acid Recovery Methods", pp. 48–59, 1958, Chemical Engineering Progress, vol. 54, No. 7.

Ratchford et al., "Extraction of Lactic Acid From Water Solution", pp. 778–781, Industrial and Engineering Chemistry, vol. 43, No. 3.

Ricker et al., "Solvent Extraction For Treatment Of Wastewaters From Acetic–Acid Manufacture," pp. 204–209, 1978, The American Institute Of Chemical Engineers, vol. 74, No. 178.

Tamada et al., "Extraction of Carboxylic Acids With Amine Extractants. 1. Equilibria And Law Of Mass Action Modeling", pp. 1319–1326, 1990, Ind. Eng. Chem. Res., vol. 29, No. 7.

Tamada et al., Extraction Of Carboxylic Acids with Amine Extractants. 2. Chemical Interactions and Interpretation of Data, pp. 1327–1333, 1990, Ind. Eng. Chem. Res., vol. 29, No. 7.

Tamada et al., Extraction of Carboxylic Acids with Amine Extractants. 3. Effect of Temperature, Water Coextraction, and Process Considerations, pp. 1333–1338, 1990, Ind. Eng. Chem., Res., vol. 29, No. 7.

Terrill et al., Separation of Closely Boiling Mixtures By Reactive Distillation 1. Theory, pp. 1062–1071, 1985, Ind. Eng. Chem. Process Des. Dev., vol. 24, No. 4.

Watson, "Composition of Lactic Acid. Production of a Highly Concentrated Acid", pp. 399–401, 1940, Industrial and Engineering Chemistry, vol. 32, No. 3.

Wise, "Biopolymeric Controlled Release Systems", pp. 3–28, 1984, CRC Press, vol. 1.

Wise, "Biopolymeric Controlled Release Systems", pp. 187–199, 1984, CRC Press, vol. 2.

Wise et al., "Lactic/Glycolic Acid Polymers", pp. 237–270, Dynatech R/D Company, Cambridge, Mass., U.S.A.

Wislicenus, "on the Optically Active Lactic Acid of Sarcolactic Liquid, the Paralactic Acid", pp. 318–319, 1873, Liebigs Ann. Chem. vol. 167.

PURIFYING CYCLIC ESTERS BY AQUEOUS SOLVENT EXTRACTION AND FURTHER PURIFICATION

CROSS-REFERENCE TO RELATED APPLICATIONS

The present application is a divisional application of U.S. patent application Ser. No. 08/473,400 filed Jun. 6, 1995, now U.S. Pat. No. 5,686,630, which is a continuation-in-part of U.S. patent application Ser. No. 08/417,597 filed Apr. 5, 1995, now U.S. Pat. No. 5,675,021, which is a continuation-in-part of U.S. patent application Ser. No. 08/128,797, filed Sep. 29, 1993, now U.S. Pat. No. 5,420,304, which is a continuation-in-part of U.S. patent application Ser. No. 07/854,559, filed Mar. 19, 1992, now U.S. Pat. No. 5,319,107, the disclosures of which are incorporated herein by reference in their entirety.

FIELD OF THE INVENTION

The present invention relates to processes for the production, recovery and purification of cyclic esters and to cyclic ester compositions. In a particular embodiment, the invention relates to the production, recovery and purification of lactide and lactide compositions.

BACKGROUND OF THE INVENTION

Cyclic esters are useful in a variety of applications. For example, cyclic esters derived from hydroxycarboxylic acids are useful in the preparation of environmentally biodegradable plastic materials, and for plastic materials which resorb when used in medical applications. Particularly useful are those polymers which are derived from α-hydroxycarboxylic acids, such as lactic acid, because they can be degraded over time by hydrolysis under most environmental conditions. The resulting hydroxy acid units (e.g., lactic acid) or oligomers thereof are then readily taken up by microorganisms in the environment and converted to carbon dioxide and water aerobically or carbon dioxide and methane anaerobically.

Cyclic esters, such as cyclic esters of hydroxycarboxylic acids can be produced through a number of mechanisms; however, such cyclic ester products typically contain multiple undesirable impurities. Such impurities can degrade cyclic esters in the product, resulting in short shelf life of the cyclic esters produced. For example, free acid and water in a cyclic ester composition can propagate hydrolyzing of the cyclic ester bonds, degrading the cyclic ester back into hydroxycarboxylic acids or other degradation products. In addition, impurities in the cyclic ester composition can interfere with both the rate of polymerization of the cyclic ester and the molecular weight, thereby prohibiting the formation of desirable higher molecular weight polymerization products. Accordingly, there is a need to obtain substantially pure cyclic esters, which are substantially free from impurities which degrade the compounds or interfere with subsequent chemical reactions, such as polymerization of the cyclic esters into high molecular weight polymers.

Several processes are known to purify synthesized cyclic ester compositions. Such processes include solvent crystallization, solvent scrubbing, solvent extraction, distillation, melt crystallization and sublimation. Although satisfactory results can be obtained in controlled laboratory conditions, many processes are difficult to operate on a commercial scale because they are complex or have impractical operating parameters. In addition, such processes may require high energy costs, high equipment costs or high reagent costs. Moreover, machinery may not be available for implementing these processes on a commercial scale.

Other processes are commercially unacceptable because the cyclic esters being purified may degrade due to the residence time or temperature constraints of the process, resulting in poor purity. Further, some processes provide low yields, making them economically unsuitable.

Accordingly, there is a need for inexpensive, reliable methods for purifying cyclic esters. In particular, there is a need for methods of obtaining cyclic esters of sufficient purity for use in producing high molecular weight polymers. Furthermore, there is a need for methods of purifying cyclic esters that allow for recovering all isomeric forms of the cyclic esters.

SUMMARY OF THE INVENTION

The present invention is directed to a process for producing a cyclic ester by the steps of (a) providing a feedstream comprising an organic solvent and compounds selected from the group of a single hydroxycarboxylic acid or its ester, salt or amide and oligomeric species thereof; (b) removing water from the feedstream to form a product stream which includes the cyclic ester, wherein the concentration of pentamers and higher oligomers in the product stream is less than about 20% by weight of the reaction mixture during the process; and (c) introducing an aqueous solvent into the product stream and allowing the product stream to separate into a first phase comprising cyclic esters and a second phase comprising the aqueous solvent and impurities.

In another embodiment, the present invention is directed to a process for the purification of cyclic esters in a composition comprising cyclic esters, an organic solvent and impurities. The process includes introducing an aqueous solvent into the composition and thereafter allowing the composition to separate into a first phase which includes the cyclic esters and organic solvent and a second phase which includes the aqueous solvent and impurities. In one embodiment, the amount of aqueous solvent introduced into the composition is less than about 3% based on the weight of the composition above the mutual solubility limit of water in the organic solvent. In another embodiment, the amount of aqueous solvent introduced into the composition is less than an amount necessary to effect hydrolysis of oligomeric XA species in the composition.

A further embodiment of the invention includes a process for purification of cyclic esters in a composition which includes cyclic esters, an organic solvent and impurities. This process includes introducing an aqueous solvent into the composition and allowing the composition to separate into a first phase comprising the cyclic esters and organic solvent and a second phase comprising the aqueous solvent and impurities. The process further includes contacting the first phase with a first adsorbent to remove impurities.

The various embodiments of the present invention allow for the effective production, recovery and purification of cyclic esters by providing processes which can be efficiently integrated. For example, the use of a water-assisted separation purification step allows for the upstream use of a wider selection of cyclic ester production solvents, as well as reduces the load of impurities to be removed in subsequent purification steps.

DETAILED DESCRIPTION OF THE PREFERRED EMBODIMENT

Figure 1:
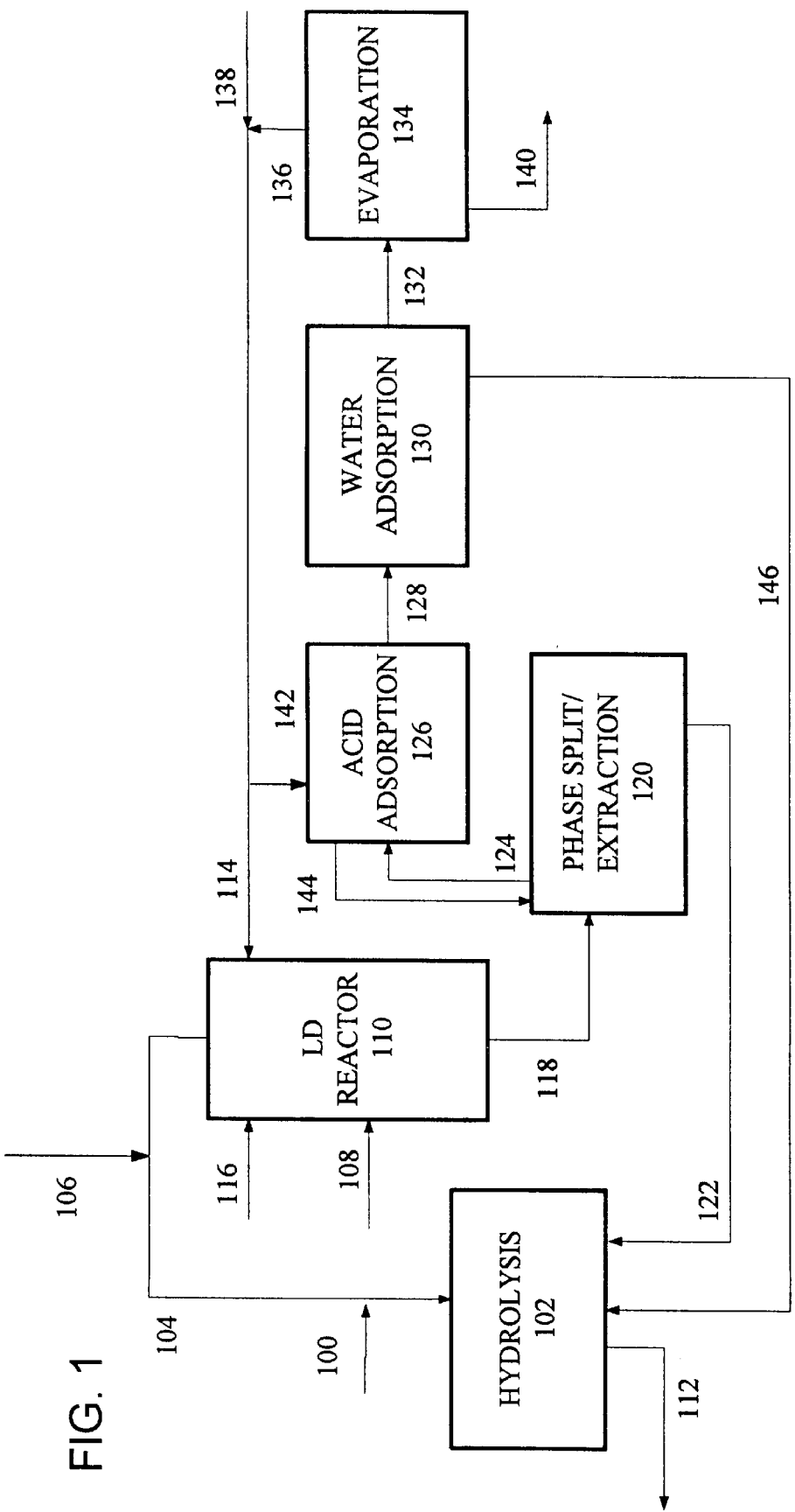
FIG. 1 is a flow diagram of an embodiment of an integrated cyclic ester production and purification process.

The present invention has utility in the production and purification of cyclic esters. Such compounds are useful for the production of polymers. For example, a cyclic ester such as lactide is useful in the production of polylactic acid. In particular, the present invention relates to production and purification of cyclic esters substantially free of impurities that can degrade the cyclic esters or interfere with the polymerization of the cyclic esters into high molecular weight polymers.

The process of the present invention involves the production and purification of cyclic esters derived from hydroxycarboxylic acids, hydroxycarboxylic acid esters, hydroxycarboxylic acid salts, or hydroxycarboxylic acid amides. The term "derived from" refers to the cyclic ester being produced by reactions in which these components or products of these components are reactants. Cyclic esters can be formed by converting an ester formed from any two hydroxycarboxylic acids, esters, salts, or amides thereof, into a cyclic diester. Cyclic esters can also be intramolecular esters or a cyclic monoester, such as lactones. Cyclic esters are referred to herein as XD. $X_1A$ refers to a hydroxycarboxylic acid, hydroxycarboxylic acid ester, hydroxycarboxylic acid salt, or hydroxycarboxylic acid amide. $X_2A$ refers to a linear dimer molecule of an $X_1A$ molecule. $X_3A$ refers to a linear trimer molecule of an $X_1A$ molecule, and $X_nA$ refers to a linear n-mer molecule of an $X_1A$ molecule. XA without subscript denotes one or more of $X_1A$, $X_2A$, $X_3A$, and $X_4A$ or a solution containing those species. It will be understood that when X is substituted by L, the corresponding compounds based on lactic acid are meant. For example, LA refers to a lactic acid-based mixture, including $L_1A$, $L_2A$, $L_3A$ and $L_4A$, and LD refers to the cyclic dimer of lactic acid, e.g., lactide.

Cyclic esters of the present invention include those compounds described above. Preferred $X_1A$ species for production of cyclic esters include, but are not limited to, the following acids and corresponding esters, salts, or amides thereof: lactic acid, glycolic acid, tartaric acid, mandelic acid, malic acid, 1-hydroxy 1-cyclohexane carboxylic acid, 2-hydroxy-2-(2-tetrahydrofuranyl) ethanoic acid, 2-hydroxy-2-(2-furanyl) ethanoic acid, 2-hydroxy-2-phenylpropionic acid, 2-hydroxy-2-methylpropionic acid, 2-hydroxy-2-methylbutanoic acid, 2-hydroxybutanoic acid, 2-hydroxypentanoic acid, 2-hydroxycaproic acid, 2-hydroxyoctanoic acid, and mixtures thereof.

Specific cyclic ester production processes of the present invention are described in more detail below. Such production processes, however, can be production of cyclic esters by direct formation of a cyclic ester from an $X_2A$ species, such as is described in U.S. Pat. No. 5,319,107. Alternatively, production of cyclic esters can be by other known methods, such as depolymerization of linear esters of lower molecular weight or synthesis by reactions of α-halo salts of carboxylic acids.

PURIFICATION OF CYCLIC ESTERS

Adsorption Treatment

The present invention includes the removal of impurities from a feed material containing cyclic esters. Such impurities include, for example: water, XA (e.g. free acids), metal ions, mineral acids, cyclic ester synthesis catalysts and associated catalyst degradation products, and typical fermentation acids and alcohols such as formic acid, acetic acid, propionic acid, butyric acid, ethanol and butanol, all of which can contribute to the degradation of cyclic esters or interfere with subsequent polymerization of cyclic esters into useful high molecular weight polymers.

The feed material can also include a solvent in which cyclic esters have good solubility, but which does not degrade the cyclic esters such as by being reactive with cyclic esters. Such solvents include those solvents used in cyclic ester production and recovery as described below. Examples of such solvents include, but are not limited to, xylene, toluene, benzene, anisole, methyl isobutyl ketone (MIBK), isopropyl ether and mixtures thereof, and a preferred solvent comprises xylene. Solvents which are not preferred because of being reactive with cyclic esters include alcohols, organic acids, esters and ethers containing alcohol, peroxide and/or acid impurities, ketones and aldehydes with a stable enol form and amines.

The relative concentrations in the feed material of the cyclic esters, impurities, and solvent depend upon the process used for producing the cyclic esters. Typically for direct synthesis of cyclic esters from $X_2A$, the feed material will contain from about 0.5 to about 10% by weight cyclic esters, less than about 10% by weight impurities, and from about 80 to about 99% by weight solvent. The impurities generally include less than about 1% by weight water and less than about 10% by weight hydroxycarboxylic acid and its ester, salt and amide.

In the purification method of the present invention, the feed material is subjected to an adsorption step in which at least one impurity in the feed material is adsorbed from the feed material by an adsorbent, thereby concentrating and purifying the cyclic ester component of the feed material. The term "adsorption" refers to the attraction or interaction between an impurity in a feedstream and an adsorbent. Preferably, this attraction or interaction between an impurity and an adsorbent is a non-covalent attractive force which is reversible. Such attraction, for example, can be based on charge differences or differences in charge distribution between the adsorbent and the impurity such as is the case in the capture of a molecular species by an ion exchange resin. Included in this definition is the concept of ion exchange in which charged species are reversibly exchanged on the surface or within the structure of an adsorbent. As discussed in more detail below, in the process of the present invention the resulting purified solution which contains purified cyclic esters is then treated by a post-adsorption treatment, such as to recover the cyclic esters in a solid form or to use the cyclic esters directly such as by polymerization.

Adsorbents suitable for use in the present invention include ion exchange resins, molecular sieves, alumina, silica gel, activated carbon, clays and other adsorbents known in the art. Preferred adsorbents are ion exchange resins, molecular sieves, silica gel, activated carbon and clays, and particularly preferred adsorbents include ion exchange resins and molecular sieves.

Selection of a specific adsorbent for a particular process depends on the type of impurity which is to be removed from the feed material. For example, if the impurity is an XA acid, it is generally desirable to remove the impurity from the feed material by contacting it with either a weak or a strong anion exchange resin. Preferably however, to remove acid impurities such as XA from feed material, it is desirable to use weak anion exchange resins. Weak anion exchange resins can achieve acceptable rates of removal of impurities while also allowing relatively easy regeneration of the resin. For example, suitable commercially available weak anion exchange resins are sold by Reilly Industries, Inc., Indianapolis, Ind., under the product designation REILLEX® 425 and by Rohm and Haas, Philadelphia, Pa., under the product designation AMBERLYST® A-21. REILLEX® 425 is a macroreticular bead form of crosslinked poly-4-vinylpyridine. AMBERLYST® A-21 is a divinylbenzene-styrene based resin with tertiary amine functional groups.

To remove water as an impurity from the feed material, the feed material can be contacted with an adsorbent selected from the group consisting of molecular sieves, alumina and silica gels, and most preferably molecular sieves. As used herein, the term "molecular sieve" refers to an adsorbent having structural characteristics which promote adsorption of impurities and which excludes the adsorption of cyclic esters.

For the removal of XA amides as impurities, it is generally desirable to use complexing resins. For the removal of XA salts as impurities, it is generally desirable to use a strong anion exchange resins.

For removal of alcohols as impurities, it is generally desirable to use molecular sieves or ion exchange resins. Since these adsorbents have stronger affinities for the more polar impurities in the feed such as XA and $H_2O$, it is generally desirable to remove these more polar impurities from the feed prior to alcohol adsorption treatment. Removal of these more polar impurities allows the lower affinity alcohols to adsorb on these materials without having to compete with more polar high affinity impurities in the feed, thus increasing the capacity of these alcohol adsorbents.

The step of contacting a feed stream with an adsorbent can be conducted at any suitable temperature such that acceptable rates of adsorption occur. Preferably, the temperature of the feed stream is between about 0° C. and about 100° C., and more preferably between about 25° C. and about 45° C.

In a preferred embodiment of the adsorption process of the present invention, feed material is subjected to a first adsorption to remove a first impurity and then is subjected to a second adsorption to remove a second impurity. Optionally, additional adsorption steps can be conducted. The purified cyclic ester-containing feed material can then be subjected to post-adsorption treatment to recover cyclic esters as described below. The use of such multi-step adsorption processes is particularly useful in the present invention because they provide for the removal of multiple impurities from the feed material. For example, a first adsorption can be conducted to remove impurities such as XA from the feed material and a second adsorption can be conducted to remove water from the feed material, or vice versa. A third adsorption can optionally be conducted, for example, to remove alcohols if present. Further, a fourth adsorption can optionally be conducted, for example, with a carbon filter to remove color bodies if present. In the case of multi-step adsorption, the steps can be conducted in any desirable order.

In a preferred embodiment, adsorbents suitable for use in the present invention are heat stable at temperatures above about 100° C., and more preferably, above about 130° C. The term "heat stable" refers to the ability of an adsorbent to retain its capacity, when subjected to high temperatures, to adsorb impurities upon return to normal adsorption operating temperatures. For example, while REILLEX® 425 resin may be used for adsorbing impurities at temperatures of less than about 100° C., it is thermally stable at temperatures up to about 260° C. Thus, such resins are particularly useful in a purification process in which the resin is regenerated at elevated temperatures after adsorption at normal operating temperatures.

Preferred adsorbents of the present invention include adsorbents which do not degrade cyclic esters in the feed material. For example, processes of the present invention are conducted with adsorbents and under conditions such that preferably less than bout 25% by weight of cyclic esters are degraded by contact with the adsorbent, more preferably less than about 10% by weight and most preferably less than about 5% by weight. In this regard, an adsorbent such as an ion exchange resin is preferred over an adsorbent such as alumina which can degrade cyclic esters.

Adsorption steps of the present invention can be accomplished using a variety of apparatus such as a fixed adsorbent using packed columns or beds as are known in the art. Some examples of these types of systems are: moving bed, simulated moving bed, two column arrangements and three column arrangements. In addition, it is possible to use an adsorbent which is loose in the feed material such as being a slurry formed from the adsorbent material and the feed material.

Adsorption operations of purification processes of the present invention can be conducted in either batch or continuous modes. It is preferred, however, that the such adsorption methods be operated continuously.

In a further embodiment of the present invention, the adsorption treatment can include adsorption treatment of an evaporated solvent stream produced by evaporation prior to a main crystallization purification process. For example, it is known that cyclic esters can be purified by a variety of crystallization processes, including solvent crystallization. Prior to a conventional solvent crystallization process, a cyclic ester-containing product stream which additionally includes impurities and solvent can be concentrated by evaporating a portion of the solvent. In such an instance, the evaporated solvent produced thereby includes small amounts of cyclic ester and impurities. Thus, the evaporated solvent stream can be purified by adsorption treatment as broadly described herein prior to reuse of the evaporated solvent stream in other unit operations. For example, the evaporated solvent stream can be subjected to one or more adsorption steps, such as an acid adsorption step and a water adsorption step, to remove acid and water impurities. The resulting solvent stream would include solvent and remaining cyclic esters which are not removed by the adsorption steps. Such a stream can then be reused in other operations in an overall recovery process. For example, such a solvent stream can be used as solvent for a solvent crystallization process of the concentrated cyclic ester composition resulting from the initial evaporation of solvent. Such a crystallization can be a multiple stage recrystallization process.

The solvent resulting from the solvent crystallizations can be further recycled to other points in the overall recovery and purification process for cyclic esters. For example, such a solvent stream, which would include impurities and cyclic ester, can be recycled to a liquid-liquid phase separation step prior to concentration of a cyclic ester-containing product stream.

Post-Adsorption Treatments

As noted above, subsequent to purification by adsorption, a variety of post-adsorption treatments can be employed to either recover the cyclic esters in some solid form or to directly polymerize cyclic esters. Recovery processes include concentration processes, drying processes and further purification, among others known in the art.

In one embodiment of recovery, cyclic esters can be recovered by spray drying the purified feed material in order to recover the cyclic esters in powder form. Spray drying involves the atomization of the purified feed material in countercurrent flow with a drying, preferably dry and inert, gas to drive off solvent from the purified feed material. Typically, spray drying is conducted at elevated temperatures. Spray drying results in the production of a powder which can be packaged and sold and is suitable for use such as in the production of polymeric material.

In another post-adsorption treatment, the purified feed material can be concentrated, such as through the use of an evaporator. For example, the purified feed material can be first run through an evaporator unit in which solvent is driven off. In preferred embodiments, enough solvent is driven off so that the remaining cyclic ester mixture has between about 1% and about 80% by weight solvent, more preferably between about 5% and about 50% solvent, and even more preferably between about 15% and about 30% solvent. It shall be noted that solvent which is removed during concentration can be recycled, for example, back to other stages in an overall process, including, for example, recovery of $X_1A$ prior to cyclic ester production, regeneration fluid for acid adsorption units, or directly back to cyclic ester production operations as described in more detail below. Such solvent can also be brought forward for use in subsequent recovery or purification operations, such as solvent crystallizations. After exiting the evaporator unit, the cyclic ester-containing stream can be cooled prior to additional recovery or purification operations.

After concentration, the concentrated, purified feed material can be polymerized directly or dried as a final product. In the embodiment of drying concentrated cyclic ester material, the concentrated feed material can optionally be further purified prior to drying. Drying can be accomplished by numerous methods, such as by spray drying the concentrated, purified feed material as discussed above. Further, concentrated cyclic esters can be prilled. Prilling refers to a process for pelletizing a solid material which includes melting the material and spraying the molten material, whereby droplets of the material solidify. Prilling involves the atomization of an essentially solvent free, molten purified feed material in countercurrent flow with a cooling, preferably dry and inert, gas to cool and solidify the purified feed material. Typically, prilling is conducted at near ambient temperatures. Prilling results in the production of beads which can be packaged and sold and is suitable for use such as in the production of polymeric material.

As noted, further purification of the recovered cyclic esters can be conducted before drying, such as by solvent cooling crystallization, solvent evaporative crystallization, melt crystallization, distillation, or combinations thereof. All of these methods are classified as positive purification steps since the desired cyclic ester species preferentially undergoes a phase change and is removed from the impure feedstock. In contrast, the adsorption based purification discussed above are classified as subtractive purification steps since they remove specific impurities from the impure feedstock. While the subtractive purification steps can drive the levels of impurities, such as acids, water, and alcohols to very low levels, it is possible that other undesirable species could pass through the adsorption steps and end up in the cyclic ester product if a positive purification step is not used.

For example, waxy residues commonly found in industrial grades of solvents, such as xylene, would not be removed by adsorption treatments. If the post-adsorption treatments only consisted of evaporation and spray drying or prilling, these waxy residues would end up in the cyclic ester product used for polymerization. While this particular contaminate may not affect the polymerization rate and molecular weight results, it does negatively affect assay values and appearance of the cyclic ester product both of which are commercially important. As another example, XA obtained from fermentation based processes will typically contain low levels of poorly defined contaminants which could also pass through the adsorption purification steps. For these reasons, it is often desirable to include one of these positive purification steps in the post-adsorption treatment processing.

There are several advantages for using the adsorption steps prior to the post-adsorption purification treatment steps. For example, in the instance of post-adsorption crystallization, larger crystals can be produced because crystal size usually increases when crystallizations are performed on solutions with low levels of impurities. Large crystals are easier to handle, have lower surface area to volume ratios, and are generally more pleasing to potential customers of cyclic ester products. As another example, by removing the XA and water by adsorption prior to positive purification steps, one can use higher temperature processing in the post-adsorption treatments without significant degradation of the cyclic ester product. Thus, for example, high temperature processing steps like prilling and distillation can be used with less degradation than if significant XA or water were present. The following discussion of positive purification type post-adsorption treatments steps is ordered by increasing levels of high temperature processing.

In one embodiment the concentrated feed material can be solvent crystallized to obtain a purified cake and then further dried to remove residual solvent. There are numerous configurations of equipment which can be used for both solvent cooling and solvent evaporative crystallization. Those familiar with the art will be able to pick an appropriate configuration for a given application.

Solvent used in solvent crystallization performs a number of functions during the crystallization process. By use of a solvent, crystallization can be conducted at lower temperatures than if no solvent is present. In addition, the presence of solvent reduces viscosity of the system thereby making material handling and pumping easier and improving heat transfer. Further, the presence of the solvent can result in a purer crystallization process by providing a medium to contain impurities such as $X_1A$ and oligomers of $X_1A$ during crystallization. Thus, upon subsequent separation of crystals from the crystallization mixture, impurities such as $X_1A$ and oligomers of $X_1A$ can more readily separate with the liquid stream, rather than adhering to crystals.

The liquid stream resulting from separating the cyclic ester crystals can be further treated for additional recovery of cyclic esters from the liquid stream. Additionally, the liquid stream can be treated for recycle of $X_1A$ and oligomers of $X_1A$ present in the liquid.

In an alternative embodiment, the cyclic esters can be further purified by melt crystallization. In a melt crystallization process, the cyclic ester material is subjected to temperatures sufficient to melt the cyclic esters without the presence of significant amounts of solvent. The melted material is then cooled and a portion of the material is allowed to crystallize. There are several configurations of equipment for melt crystallization. Those familiar with the art will be able to pick an appropriate configuration for a given application.

It should be noted that melt crystallization has a number of particular advantages over solvent crystallization processes. For example, because the volume of material being handled is significantly smaller in the absence of a solvent, smaller sized equipment is needed to obtain the same production. In addition, it has been found that larger crystal sizes are obtained by melt crystallization. Larger crystals are typically more pure than smaller crystals due to higher volume to surface ratios, thereby reducing surface area available for adherence of impurities.

A further embodiment of the present invention when post-adsorption treatment includes an additional purification step such as crystallization is the selective recovery of cyclic esters from a mixture which includes more than one isomeric species of the cyclic ester. This process includes selectively crystallizing one of the isomeric species of the cyclic ester and recovering that isomeric species. This recovery method is suitable when $X_1A$ is a chiral molecule and, thus, has isomeric forms. For example, lactic acid is a chiral species of $X_1A$. There exist two optical isomers of lactic acid, L-lactic acid and D-lactic acid. Consequently, lactide can be either L-LD (a lactide molecule formed from two L-lactic acid molecules), D-LD (a lactide molecule formed from two D-lactic acid molecules), meso-LD (e.g., M-lactide, a lactide molecule formed from one L-lactic acid molecule and one D-lactic acid molecule), or D,L-LD (an intermolecular species consisting of one L-LD molecule and one D-LD molecule). The different species of lactide have different melting points. Meso-LD has the lowest melting point of 52.8° C., isomerically pure D-LD and L-LD both have melting points of 98.7° C., and pure D,L-LD has the highest melting point of 128° C.

For example, isomeric species of a given XD molecule having higher melting points than other isomeric species can be selectively crystallized in a melt crystallization process. By forming a melt of the entire cyclic ester mixture, and crystallizing the higher melting point species at a temperature above the melting point of the lower melting point cyclic ester species, the higher melting point species can be selectively crystallized. Alternatively, an isomeric species of a given XD molecule having higher melting points than other isomeric species usually will be less soluble in any given solvent. By conducting a solvent crystallization at a temperature above the solubility limit of the lower melting point cyclic ester species, the higher melting point species can be selectively crystallized.

Subsequently, upon recovery of the crystals, for example, by centrifugation, the resulting solid will have the higher melting point isomeric species plus residual amounts of the lower melting point isomeric species. The cake from this crystallization can be potentially used as one of the two XD feeds to an XD polymerization step. The other feed to the XD polymerization step could be recovered from the liquid residue produced by the selective crystallization step using various techniques such as spray drying, prilling, crystallization, distillation, evaporation, or combinations thereof.

It should be noted that selective crystallization, as discussed above, will not achieve 100% selectivity. Thus, in the example discussed above, the first crystallized fraction may contain residual amounts of the lower melting point species. Likewise, the second recovered fraction will contain significant amounts of the higher melting point species. However, as long as the desired ratio of optical isomers for the polymerization operations is between the isomer contents of the two XD products, a simple blending operation can be used to adjust the actual ratio of optical isomers in the XD feedstock for the polymerization operations. This is significant since it is one possible method for control over the optical isomer content of the XD based polymers, which is what controls the physical and degradation properties of many XD based polymers.

In an alternative embodiment of post-adsorption processing, the cyclic esters can be further purified by distillation. Typically, a center cut would be taken as product in a batch distillation process. Alternatively, a center cut could be generated in a continuous distillation system using a standard two column method or a one column method utilizing a sidestream draw for the product stream.

The product from the distillation process can be used directly in XD polymerization. Alternatively, the product could be spray dried or prilled, and then stored for later use.

A further embodiment of the present invention when post-adsorption treatment includes an additional distillation purification step is the selective isomeric recovery of the cyclic esters. For example, the boiling points of L-LD, D-LD, and D,L-LD are all very close and distillation would not be used to separate these species. However, the boiling point of M-LD is significantly lower than the boiling points of the other isomers, thus a distillation system could be designed to produce two product fractions with significantly different isomer contents. This represents another method for controlling the isomer content of the XD polymerization unit feedstock, thus controlling the isomer content at the XD based polymers.

It should be clear from the previous discussion that one of the major issues in cyclic ester recovery processes is how to provide control of the isomer content of the cyclic ester products used for polymerization. One major advantage of the adsorption treatments is that they are non-stereospecific purifications, thus the isomer content of the product of the adsorption treatment steps is the same as the isomer content of the feed to the adsorption treatment steps. All of the non-purification based post-adsorption treatment steps discussed here are also non-stereospecific processing steps. Thus for example, if one were to use concentration followed by spray drying for the post-adsorption treatment steps, the isomer content of the cyclic ester product would be determined by the isomer content of the feed to the adsorption purification steps. This outcome is significant since isomer control can easily be performed by either controlling the isomer ratio of the XA feed to the synthesis reactor, or by controlling the degree of racemization occurring in the XD synthesis reactor by changing temperature, residence times, levels of racemizing agents added to the reactor, etc., or by combinations of XA feed isomer control and XD synthesis reactor conditions.

The purification based post-adsorption treatment steps discussed here have varying degrees of stereospecificity. Crystallization based methods generally produce purified products containing only one or two stereoisomers of the cyclic esters. As described previously, the other isomers can be recovered from the liquid residues of the crystallization steps. Alternatively, one could use a blocked operation mode with a crystallization based method in which the entire XD synthesis and recovery operation is timeshared between producing the various desired isomers of the cyclic ester products. The distillation based methods are generally not as stereospecific as the crystallization methods. For example, the boiling point of M-LD is close enough to the other isomers that one could design for either a one product or two product system. The isomer content of the one product system would essentially be the same as the isomer content of the feed to the adsorption unit. The two product distillation system described previously would allow one to individually control the isomer content of multiple polymerization line operating in parallel.

Adsorbent Regeneration

The purification processes of the present invention can also include regeneration of the spent adsorbent wherein the used adsorbent is treated in order to remove or "desorb" at least a portion of the adsorbed impurity and subsequent reuse of the regenerated adsorbent for adsorption. Numerous regeneration techniques are suitable, and depend upon the type of adsorbent being used. Generally, regeneration requires contacting the adsorbent with a fluid (gas, liquid, or supercritical) under conditions which cause the adsorbed impurities to desorb from the adsorbent into the fluid.

In the instance where the impurity being desorbed from an adsorbent is water being desorbed from, for example, a molecular sieve, the desorption step is a drying process. Such drying processes can be accomplished by drying the adsorbents using known techniques. For example, a typical drying process includes contacting the adsorbent with a hot, preferably inert gas to remove the entrapped water. Drying can be conducted at any suitable temperature and is preferably conducted at a temperature between about 175° C. and about 300° C. depending upon the type of molecular sieve being used. Drying can optionally be carried out in a reduced pressure environment to accelerate the evolution of water.

In the instance where the impurity being desorbed from an adsorbent includes an XA species and/or XA oligomers, the desorption fluid can be an organic solvent, an aqueous solution or a hot inert gas. For example, a solvent which was the solvent originally in the feed material can be used for desorption of impurities from the resin. Alternatively, other solvents in which the impurities are soluble are acceptable for desorption and can include, but are not limited to those identified above in the discussion regarding adsorption treatment. A preferred desorption solvent is xylene.

In an optional embodiment, the desorption fluid can be heated prior to contact with the adsorbent to improve its effectiveness. Contacting the heated desorption fluid with the adsorbent causes an increase in the temperature of the adsorbent. This in turn causes a decrease in the adsorption equilibrium so a portion of the absorbed XA species will desorb from the adsorbent. The amount of XA desorbed by heating will depend upon the amount of the adsorbent temperature rise and the temperature sensitivity of adsorption equilibrium for a given adsorbent and solvent combination. Typically, the adsorption equilibrium for weak absorbents such as weak anion exchange resins are more sensitive to temperature changes when compared to strong absorbents.

Other means can be used to heat the adsorbent. For example, if the adsorbent is installed in the tubes of a shell and tube heat exchanger, the adsorbent can be heated by applying steam or other heat transfer media to the shell. In this configuration, a desorption fluid still has to be used to carry the XA species away from the resin, however the amount of desorption fluid required is generally less than the adiabatic heating cycle described in the previous paragraph.

Temperatures for regenerating adsorbents are generally in the range of about 100° C. to about 260° C. Suitable temperatures can be selected such that acceptable rates of desorption are achieved without causing substantial degradation or loss of adsorption capacity. In the event of a desorption temperature being in excess of the boiling point of the desorbing fluid, the desorption can be conducted under pressure.

The main advantage of the thermal regeneration methods is that there are no waste products formed except for XA species in a solvent of choice. Thus the regeneration effluent streams can easily be recycled to several places in the cyclic ester synthesis process with little or no additional treatment. Thermal regeneration methods, however, are fairly gentle and do not desorb strongly adsorbed species from the resin. These strongly adsorbed species typically would include metal ions, mineral acids, and catalyst degradation products such as sulfonated xylene. Over time, these strongly adsorbed species may decrease the XA capacity of the resin to the point where a more powerful desorption technique is required.

Chemical regeneration methods can also be used to desorb the XA species from the resin. These methods use more powerful desorption agents when compared to the thermal methods. In chemical regeneration, a caustic solution is used to desorb the XA and other strongly adsorbed species from the resin. The caustic solutions can either be aqueous based or alternatively the caustic can be dissolved in polar organic solvents such as methanol. While chemical methods are more powerful, their use raise some additional issues. First, at the end of the desorption cycle the resin will contain a caustic solution which has to be removed from the resin prior to the next adsorption cycle. Since these solutions contain caustic, water, and/or alcohols, all of which are detrimental in either cyclic ester recovery or polymerization processes, fairly rigorous removal of these species is required. Second the effluents from the caustic regeneration will generally contain salts which must be treated prior to recycling or disposal. This treating equipment can be a separate set of equipment located within the XD production and purification unit. Alternatively, if the XA feedstock to the synthesis reactor is derived by acidifying a fermentation broth, the regeneration effluent can be sent to the acidification step in fermentation recovery for an integrated XA and XD production facility.

Combinations of the thermal and chemical regeneration methods could be used. For example, thermal regeneration could be used in many regeneration cycles until the adsorption capacity of the resin falls below a desired minimum value. Then, one or more chemical based regeneration cycles would be used to restore resin capacity. Then, thermal regeneration cycles could be used again until the adsorption capacity falls below the desired performance.

In another aspect of the invention, various guard column configurations can be used upstream of a thermally regenerable XA adsorption unit. The purpose of the guard column is to selectively adsorb the strongly adsorbing species from the feed and allow the XA species to pass through to the thermally regenerable XA adsorption column. This would greatly decrease the frequency at which the XA adsorption column would have to use chemical regeneration methods. Another advantage of this is that, since the guard column would have to be chemically regenerated anyway, the thermal stability of the resins used in the guard column is not an issue. Thus, inexpensive, high capacity resins with low thermal stability could be used for the guard column. As an example of a good candidate for the guard column resin, the AMBERLYST® A-21 resin described previously is inexpensive, has six times the capacity of the REILLEX® 425, but only has an upper temperature stability limit of about 75° C. On the other hand, REILLEX® 425 is more expensive, has a lower capacity, but is thermally regenerable at temperatures up to 260° C., thus making this resin a reasonable choice for use in the XA adsorption application.

The desorbing fluid which contains desorbed impurities can be recycled for use in other stages of an overall cyclic ester production and recovery process. The destination of such recycle streams will depend on the nature of the desorbing fluid and the impurities in it. For example, if the desorbing fluid is an organic solvent such as xylene and the impurities are XA species, small amounts of cyclic ester will be generated during the recycle process. Thus, the recycle stream can be directed to a post-cyclic ester production stage prior to adsorption. For example, as described below in more detail a cyclic ester production process (an include a phase split or extraction step after cyclic ester production and before adsorption. By recycling a regeneration stream to such a phase split/extraction step, (1) generated cyclic ester can be recovered in the adsorption purification, and (2) oligomers and XA acid species will be separated and for example, can be sent to a hydrolysis unit prior to the cyclic ester production process.

In the event the desorbing fluid is water, for example, the desorption recycle stream can be recycled directly to a hydrolysis unit prior to the cyclic ester production process. In this manner, hydrolysis of oligomers in the recycle stream can be initiated by the water thereby reducing the required capacity of the hydrolysis unit.

In continuous processes which involve adsorbent regeneration, two or more adsorbent columns or beds can be used in order to alternate their use to allow the continuous operation of the process. When one adsorption column or bed has reached capacity, the column or bed is taken off-line and a new regenerated column or bed is switched in for adsorption duty.

PURIFIED CYCLIC ESTER COMPOSITIONS

A further aspect of the present invention includes highly pure cyclic ester compositions. Such compositions can be produced by the methods of the present invention. Cyclic ester compositions such as lactide are unstable in the presence of water and acid. In the presence of water, lactide can be hydrolyzed to $L_2A$ which can be hydrolyzed to $L_1A$. Further, free acid can catalyze the hydrolysis reaction. Thus, cyclic ester compositions in accordance with the present invention having low levels of water and free acid are highly advantageous because of the resulting stability during shipping and storage and extended shelf life.

For every 10 ppm of water in a lactide product which is consumed by hydrolysis reactions, a free acid increase of 0.56 meq free acid/kg LD is incurred. Typical specifications for commercial lactide are a maximum of 200 ppm of water and a maximum of 1 meq free acid/kg LD. Thus, even for lactide products which initially meet product specifications, more than enough water can be present to generate free acid levels above acceptable levels during subsequent storage and processing. Therefore, it should be clear that current commercial products do not have a long shelf life because with such high levels of water, the hydrolysis reactions will cause the free acid levels to rise above specification levels in a relatively short time.

In accordance with the present invention, cyclic ester compositions are provided which have water contents of less than about 200 parts per million (ppm), more preferably less than about 60 ppm and most preferably less than about 20 ppm. Further, in accordance with the present invention, cyclic ester compositions are provided which have free acid contents of less than about 1 milliequivalent per kilogram of cyclic ester (meq/kg), more preferably less than about 0.10 meq/kg and most preferably less than about 0.04 meq/kg. As noted above, water and free acid in cyclic ester compositions interact to degrade cyclic esters. Thus, the present invention includes cyclic ester compositions having both low water and low acid levels as are identified above.

A further aspect of the cyclic ester compositions of the present invention includes a packaged cyclic ester product which is highly impermeable to water because of the extreme water sensitivity of contained cyclic ester products. Such products have low water and acid contents and are packaged in packages which prevent significant amounts of water from passing into the interior of the package containing the cyclic ester composition. In particular, cyclic ester compositions of the present invention are packaged in packages having water vapor transmission rates less than about $0.1 \text{ g}/(100 \text{ in}^2)$ (24 hr), more preferably less than about $0.01 \text{ g}/(100 \text{ in}^2)$ (24 hr), and most preferably less than about $0.001 \text{ g}/(100 \text{ in}^2)$ (24 hr) at 100° F. and 90% relative humidity.

Suitable packages and packaging techniques to meet the requirements identified above are known to those skilled in the art. For example, high quality foil-LDPE laminates can have water vapor transmission rates as low as $0.006 \text{ g}/(100 \text{ in}^2)$ (24 hr) at 100° F. and 90% relative humidity. Metallized films are also known to have low water vapor transmission rates. Packaging systems using double bagging with a desiccant placed between the bags can be used or even higher water vapor barrier packaging systems such as metal containers or glass containers can also be used. In addition, storage techniques such as reducing the relative humidity of the external air exposed to the package and/or reducing the storage temperature can further reduce degradation of cyclic ester product.

POLYMER COMPOSITIONS

A further aspect of the present invention includes the production of high molecular weight polymers from cyclic esters under acceptable polymerization conditions. It is known that under extreme conditions of low polymerization temperatures and long polymerization times, high molecular weights of cyclic ester polymers, such as polylactic acid can be achieved. Attempts at polymerization at high temperatures over shorter time frames, however, produce lower molecular weight polymers. It is recognized that impurities in cyclic ester starting materials exacerbate the problem of limited molecular weights at commercially desirable polymerization conditions. It is also recognized that impurities in cyclic ester starting material decrease the rate of polymerization thus increasing the reaction time required to attain a given conversion. Furthermore, it is also recognized that the degree of mixing which occurs during polymerization has a dramatic effect on the reaction rate, with higher degrees of mixing giving significantly faster rates of polymerization. It has been determined that by using, for example, highly pure cyclic ester compositions of the present invention, high molecular weight polymers can be produced at commercially acceptable conditions.

In view of the above, a further aspect of the present invention includes a process for the production of polymers which includes polymerizing cyclic esters at a temperature greater than about 150° C. for less than about 30 hours, whereby a degree of polymerization of the resulting polymeric composition is greater than about 1,700 where XD is the monomer basis for defining degree of polymerization. In further embodiments of this process, the temperature can be greater than about 160° C. and most preferably is greater than about 170° C. In still further embodiments, the polymerization time is less than about 15 hours, preferably less than about 5 hours and most preferably less than about 15 minutes. In still further embodiments of the present invention, the degree of polymerization of the resulting polymeric composition is greater than about of 2,100 and more preferably greater than about 2,800.

In preferred embodiments of the polymerization process of the present invention, the cyclic esters which are polymerized include the cyclic ester composition as described above which can be produced by the purification processes described herein.

The polymerization process of the present invention can be used to prepare high molecular weight polymers. For example, in the instance of XD being lactide, polymers having molecular weights in excess of $M_w=250,000$, more preferably molecular weights in excess of $M_w=300,000$, and most preferably molecular weights in excess of $M_w=400,000$ can be produced. In the instance of XD being tetramethyl glycolide, polymers having molecular weights in excess of $M_w=300,000$, more preferably molecular weights in excess of $M_w=360,000$, and most preferably molecular weights in excess of $M_w=480,000$ can be produced.

CYCLIC ESTER PRODUCTION

Processes Directly Converting $X_2A$ into Cyclic Esters

The cyclic ester purification process described above is suitable for purification of any composition which contains cyclic esters. Although the primary use of the process is for purification of cyclic ester-containing compositions from production processes for cyclic esters, the purification process can also be used for purification of cyclic ester-containing compositions which are from commercial sources.

Suitable cyclic ester production processes are disclosed, for example, in U.S. Pat. No. 5,319,107 and in copending U.S. Ser. No. 08/128,797, the disclosures of which are incorporated herein by reference. These disclosures generally provide for the production of cyclic esters. One preferred embodiment includes a process for producing a cyclic ester by providing a feedstream comprising XA and treating the feedstream to form the cyclic ester directly from the $X_2A$ component of XA. In another preferred embodiment, the cyclic ester production process includes (1) providing a feedstream comprising XA in a solvent, and (2) removing water from the feedstream to form a product stream comprising said cyclic ester, wherein the concentration of $X_5A$ and higher oligomers in the product stream is less than about 20 wt % of the reaction mixture during the process. A further preferred process for producing a cyclic ester includes (a) providing a feedstream comprising XA diluted in an organic solvent; and (b) removing water from said feedstream to directly form said cyclic ester from $X_2A$.

Pre-Adsorption Treatment Processes

The various cyclic ester production processes can also include one or more initial purification steps prior to adsorption purification as described above. A first such initial purification step can include performing the cyclic ester production process in such a manner that after production the reaction mixture forms two liquid phases in equilibrium to substantially separate XD from impurities. One such phase contains predominantly the XD and solvent and the second phase predominantly contains $X_1A$ and oligomers of $X_1A$. The method includes providing a recovery solvent for the cyclic ester production mixture, and the recovery solvent can be the solvent used for production of cyclic esters. It should be noted that the second phase can either include a second phase solvent or consist primarily of $X_1A$. Cyclic esters are then recovered from the first phase by adsorption treatment as described above. The cyclic ester production mixture can further include soluble esterification catalysts, such as sulfuric acid, which preferably partitions into the second phase. In this manner, the catalyst is readily separated from the cyclic ester.

Any solvent having suitable characteristics in accordance with the above-described functional parameters for a recovery solvent is suitable for use in the present process. More particularly, suitable recovery solvents include xylene, toluene, anisole, benzene, MIBK, and isopropyl ether, more preferred recovery solvents include xylene and toluene, with xylene being even more preferred.

The step of allowing phase separation of the cyclic ester production mixture into first and second phases is typically accomplished simply by allowing the mixture to cool with the cessation of any mixing or other agitation. Alternatively specialized equipment utilizing porous media or electrical fields can be utilized for the coalescing. These methods can be done either batch or continuously using standard phase separation equipment known to those skilled in the art.

In addition to separating cyclic esters and solvent from $X_1A$ and oligomers of $X_1A$ by allowing phase separation, as an alternative embodiment, an additional solvent extraction step can be conducted on the second phase which is rich in $X_1A$ and oligomers of $X_1A$. This solvent extraction step is done to recover cyclic esters and solvent which remain in the second phase. For example, solvent, which is typically the recovery solvent, and the second phase are introduced into an extraction unit to recover residual cyclic ester and solvent in the second phase.

Another embodiment of the present invention, which can be used in conjunction with post-adsorption treatments described above or independently, includes the introduction of an aqueous solvent to a mixture having cyclic esters and impurities and allowing this mixture to separate into a first phase comprising XD and a second phase comprising the aqueous solvent and Impurities, such as XA and other polar impurities, such as water, in a phase separation. In this embodiment, the amount of aqueous solvent added is less than about 3% (based on the weight of the mixture or composition) above the mutual solubility limit of water in an organic solvent in the mixture. It has been discovered that the addition of relatively small amounts of an aqueous solvent, which is a polar material, will (1) help cause a phase split when one otherwise would not occur, such as where an XD reaction mixture includes a solvent, such as anisole, and (2) provide a more favorable distribution coefficient between XD and impurities in first and second phases for solvents, such as xylene, that form separate phases even in the absence of the aqueous solvent.

Use of the above described water assisted phase separation as a purification technique for XD purification provides a number of significant advantages in integrated XD production and recovery processes. One such advantage is that, in a process for the production of XD in a non-aqueous solvent and subsequent recovery of XD, the range of solvents available for XD production is greatly expanded. By way of example, solvents which have unacceptably low distribution coefficients between XD and XA species or do not phase separate in a phase separation step but which are otherwise desirable either due to a high XD selectivity, conversion and/or productivity, such as anisole, or due to a greater environmental acceptability and/or acceptability for consumer applications, such as 2-octanone, can now be used.

Another advantage of the water-assisted phase separation process is that it can simplify subsequent recovery processes. For example, in the instance of a subsequent adsorption recovery process, the addition of an aqueous solvent in a phase separation step enhances the separation of free acid species from the XD mixture, thereby reducing the demand for removal of free acid by an adsorbent. Such a reduction reduces either the size of the adsorption units or the needed frequency of adsorbent regeneration cycles and therefore significantly reduces operating and capital costs. In the absence of the aqueous solvent addition step, the XA levels in the XD containing phase can be relatively high and require an unacceptably large adsorption unit which must be regenerated frequently. The adsorbent regeneration processes noted above can be costly, especially those relying on thermal energy consumption for adsorbent regeneration. The significant reduction in XA and other impurity levels in the XD-containing phase achieved by the addition of the aqueous solvent permits not only a lower frequency of adsorbent regeneration cycles but also a significant reduction in the amount of adsorbent used (and therefore the size of the equipment required to contain the adsorbent).

The aqueous solvent can be any water-based solvent that is nonreactive towards XD at the desired operating temperatures and concentrations in the aqueous addition and phase separation steps. The term nonreactive means that the aqueous solvent will not cause a significant amount of XD to ring-open. Preferably, less than about 10% of XD is degraded by reaction with the added aqueous solvent, more preferably less than about 5%, and most preferably less than about 1%. Suitable aqueous solvents include water and solutions containing XA from 0% to 88% by weight. More preferred aqueous solvents include water and dilute XA solutions (containing XA from about 0% to about 5% by weight), with water being even more preferred. In one embodiment of the water-assisted phase separation, the aqueous solvent includes a slipstream portion of the feedstream to a cyclic ester production unit. In this embodiment, after phase separation, the second phase comprising aqueous solvent and for example, XA species, is directed through a hydrolysis step to the cyclic ester production unit.

In one embodiment, the aqueous solvent is substantially free of XD impurities other than water. Such impurities can create problems in the later processing of the XD and its polymeric derivatives and/or the use and/or disposal of the polymeric derivatives. Impurities include single or straight-chain hydroxycarboxylic acid or its ester, salt or amide, and other impurities coming from the XA feedstock and/or side products from the XD synthesis reaction step. Alternatively, impurities can include many Metal-containing hydroxides, carbonates, and salts (e.g., hydroxides, carbonates, and salts of alkaline metals and alkaline earth metals). More preferably, the aqueous solvent includes no more than about 1% by weight single- or straight-chain hydroxycarboxylic acid or its ester, salt, or amide. The aqueous solvent further includes no more than about 1% by weight of other impurities coming from the XA feedstock and/or side products from the XD synthesis reaction step.

It should be noted that the aqueous solvent is itself an impurity that is detrimental to the stability of XD and subsequent use of XD, such as polymerization, and residual amounts of the aqueous solvent are preferably removed as discussed above in a water adsorption step. Therefore, the amount of aqueous solvent contacted with the reaction mixture to form a composition is preferably maintained at the minimum level to yield the desired phase separation performance. The amount of aqueous solvent contacted with the reaction mixture is preferably less than about 3% (based on the volume of the total reaction mixture after addition of the aqueous solvent) above the mutual solubility limit of water in the organic solvent (i.e., less than about 3% above the maximum water concentration at which water and an organic solvent in the reaction mixture are miscible), more preferably less than about 1.5%, and most preferably less than about 1% by weight based on the weight of the composition after addition of the aqueous solvent. It should be noted that the water assisted phase separation can be conducted on either a continuous or a batch basis. In the instance of a continuous process, the above values for the amount of aqueous solvent used refers to the total amount of aqueous solvent added to the total amount of XD containing composition for any given time portion during operation of the continuous process.

In another aspect, the amount of aqueous solvent added to the reaction mixture is equal to or less than an amount necessary to effect hydrolysis of oligomeric XA species in the reaction mixture in a subsequent hydrolysis operation. Thus, in this aspect of the invention, the amount of aqueous solvent added to the reaction mixture is equal to or less than an amount which provides a stoichiometric amount of water necessary for the hydrolysis of ester linkages in oligomeric XA species.

The temperatures of the cyclic ester containing composition in the water assisted phase separation step must be low enough to inhibit significant hydrolysis of the XD by the aqueous solvent and to lower the solubility of acid impurities in an organic solvent containing the XD to acceptable levels, yet be high enough to inhibit the precipitation of XD upon addition of the aqueous solvent. Preferably, the temperature in the water assisted phase separation step is less than about 80° C. and more preferably range from about 0° C. to about 60° C. and most preferably from about 25° C. to about 50° C.

The cyclic ester containing composition, which includes both cyclic esters and impurities, can also include an organic solvent. Such solvents include, but are not limited to xylene, toluene, benzene, methyl isobutyl ketone, isopropyl ether, anisole and 2-octanone, more preferably such solvents include xylene and 2-octanone, and most preferably such solvents include xylene.

Using the above-noted parameters, the XD in the composition report to the first phase and impurities report to the second phase. Preferably, the amount of XD reporting to the first phase is at least about 80%, more preferably at least about 90%, and most preferably at least about 95% by weight of the XD in the composition. The amount of impurities reporting to the second phase is at least about 60%, more preferably at least about 80%, and most preferably at least about 95% by weight of the impurities in the composition.

Prior to use of a water-assisted extraction step, as discussed above, a first extraction step can be performed without the assistance of water. Such a two-step process can acheive higher purities than a one-step extraction process.

The equipment that can be used for the extraction steps can be any of those commonly used for extraction such as mixers-settlers, mixers-coalescers, multi-stage extraction columns (plate, rotating and reciprocating disc), and membrane-based liquid-liquid extraction units.

After separation of the first phase from the second phase by the techniques described above, the first phase can be treated to purify the contained XD by techniques described above and the second phase recycled to the feedstream in the cyclic ester production process after hydrolysis. As noted above, the XD in the first phase can be further purified by adsorption, crystallization, and distillation techniques with adsorption being the most preferred technique.

After the water assisted phase separation described above, the first phase is preferably substantially free of impurities. In particular, the first phase contains less than about 100 meq free acid/kg solution, more preferably less than about 50 meq free acid/kg solution and most preferably less than about 10 meq free acid/kg solution. Further, the first phase contains less than about 2000 ppm water, more preferably less than about 500 ppm water and most preferably less than about 250 ppm water.

As noted above, the use of a water assisted phase separation provides significant advantages, however, the process involves the introduction of water into an XD product stream. While water is considered to be an impurity, the introduction of water can be well tolerated if, for example, a subsequent water adsorption step as described elsewhere is conducted. Even with the use of a water assisted phase separation step, the subsequent use of a water adsorption step can produce cyclic ester compositions with low water contents as described elsewhere herein.

Other Cyclic Ester Production Processes

Other cyclic ester production processes are known and are suitable for production of cyclic esters in the present invention. For example, another process for producing a cyclic ester includes vaporizing a portion of a feedstream comprising XA and reacting the vaporized portion of the feedstream in a reaction zone maintained at pressure and temperature conditions sufficient to maintain the vaporized portion in a vaporized state and to form cyclic esters. Cyclic esters can also be produced such as through the use of depolymerization reactions and condensation reactions utilizing α-halo salts. For example, a composition containing polylactic acid can be depolymerized in order to obtain cyclic esters through the use of a "back-biting" mechanism. In an α-halo salt reaction, a cyclic ester is produced by the reaction of α-halo salt molecules.

INTEGRATED CYCLIC ESTER PRODUCTION AND PURIFICATION

The present invention further includes an integrated process for the production of cyclic esters and purification by use of an adsorption treatment as broadly described above. A variety of such cyclic ester production processes are also described above. In a preferred embodiment, such an integrated process includes (1) providing a feedstream comprising XA in a solvent, (2) removing water from the feedstream to form a product stream including the cyclic ester, wherein the concentration of $X_5A$ and higher oligomers in the product stream is less than about 20 wt % of the reaction mixture during the process; and (3) contacting the product stream with a first adsorbent to remove at least one impurity from the product stream selected from free acid, water and mixtures thereof to form a purified product stream.

Referring now to FIG. 1, a flow diagram of one embodiment of the present invention is shown illustrating an integrated production and purification process of the present invention for the cyclic ester lactide. In FIG. 1, lactic acid 100 is fed to a hydrolysis unit 102 and combined with water 104 and an isomer control agent 106 which are also fed to hydrolysis unit 102. Lactic acid present as $L_3A$ and higher order oligomers are hydrolyzed in the hydrolysis unit 102 in order to produce a mainly $L_1A$ and $L_2A$ feed 108 to LD reactor 110. Used water 112 from the hydrolysis unit 102 is purged from the system. Lactic acid in lactic acid feed 108 to the LD reactor 110 is combined with a solvent 114 and, if required, a catalyst 116 both of which are also fed to LD reactor 110. Lactide is produced in LD reactor 110 such as by techniques described previously. Water removed in the lactide production reaction can be recycled and used as water 104 in hydrolysis unit 102 as previously described. The lactide, impurity and solvent mixture 118 produced in LD reactor 110 can then be fed to a phase split or extraction process 120 in order to initially remove impurities, (e.g., XA and XA oligomers) from the lactide and solvent mixture. The XA impurities removed 122 from the lactide, impurity and solvent mixture can be recycled back to hydrolysis unit 102. The purified lactide and solvent mixture 124 can be subjected to a first adsorption 126 to remove at least a portion of XA impurities, including acid impurities, such as through the use of an anion exchange resin. The purified lactide and solvent mixture 128 from the first adsorption can then be fed to a second adsorption 130 to remove water that may still present in the purified lactide and solvent mixture 128. The purified lactide and solvent mixture 132 from the second adsorption can then be concentrated, such as through the use of an evaporation unit 134 in which solvent 136 is driven off and can be recycled or combined with additional solvent 138 and fed to lactide reactor 110 as solvent stream 114. The concentrated, purified lactide and solvent solution 140 obtained from evaporation unit 134 can be further purified as described above, or, can be used for the polymerization of lactide into polylactic acid.

The embodiment as described in FIG. 1 also shows the regeneration of the adsorbents in the first adsorption 126 and second adsorption 130. Solvent 142, such as that used as a feed for LD reactor 110 can be contacted with adsorbent in the first adsorption apparatus 126 in order to desorb impurities on the adsorption material. The resulting solvent which contains impurities 144 can be utilized in the phase split/extraction apparatus 120 for the initial purification of the lactide and solvent mixture 118. Adsorbents used in the second adsorption 130 can also be regenerated by drying the adsorbents to obtain a water and solvent mixture 146 which can be recycled back to hydrolysis unit 102 as previously described.

Figure 2:
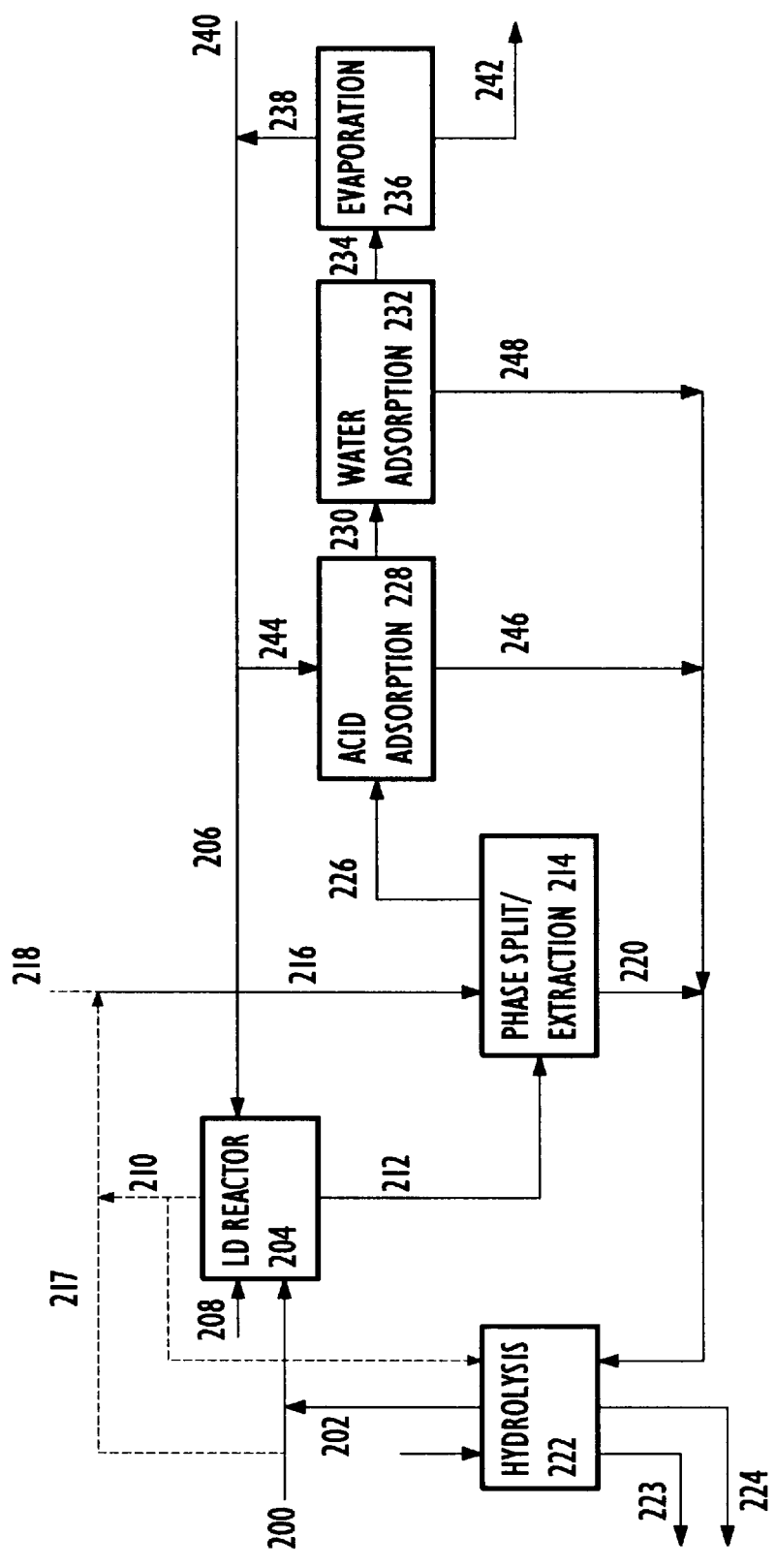
FIG. 2 is a flow diagram of another embodiment of an integrated cyclic ester production and purification process.

Referring now to FIG. 2, a flow diagram of another embodiment of the present invention is shown illustrating the addition of the aqueous solvent in the context of an integrated production and purification process of the present invention for cyclic ester lactide. Lactic acid 200 is combined with recycled lactic acid 202 and fed to the lactide reactor 204. Solvent 206 and, if required, catalyst 208 are combined with the lactic acid in the lactide reactor 204. Lactide is produced in the lactide reactor 204 such as by techniques described above. Water 210 removed in the lactide production reaction can be recycled. The lactide, impurity, and solvent mixture 212 produced in the lactide reactor 204 can then be fed to a phase split or extraction process 214 to initially remove impurities, such as XA and water, from the lactide and solvent mixture. Aqueous solvent 216 is added to the mixture during the process 214. The aqueous solvent 216 can be a portion 217 of the lactic acid 200, the water 210, clean water 218 and/or dilute lactic acid coming from other process units. The impurities 220 removed from the mixture 212 can be sent to a hydrolysis unit 222 and hydrolyzed with water 210 to form the recycled lactic acid 202. To maintain desired solvent and XA levels in the lactide reactor 204, a solvent purge 223 and an XA purge 224 can be removed from the hydrolysis unit 222. The purified lactide and solvent mixture 226 can be subjected to a first adsorption 228 to remove at least a portion of the XA impurities, such as through the use of an anion exchange resin. The purified lactide and solvent mixture 230 from the first adsorption 228 can then be fed to a second adsorption 232 to remove water and aqueous solvent that may still be present in the purified lactide and solvent mixture 228. The purified lactide and solvent mixture 234 from the second adsorption can then be concentrated, such as through the use of an evaporation unit 236 in which solvent 238 is driven off and can be recycled or combined with additional solvent 240 and fed to the lactide reactor 204 as solvent stream 206. The concentrated, purified lactide and solvent solution 242 obtained from evaporation unit 236 can be further purified, as described above, or can be used for the polymerization of lactide into polylactic acid.

The embodiment in FIG. 2 also shows the regeneration of the adsorbents in the first adsorption 228 and second adsorption 232. Solvent 244 can be contacted with the adsorbent in the first adsorption apparatus 228 to desorb the XA on the adsorption material. The resulting solvent 246, which contains desorbed XA, can be combined with the impurities 220 and sent to the hydroyzing unit 222. Adsorbents used in the second adsorption can be regenerated as discussed above to obtain water 248 which can be recycled back to the hydrolysis unit 222 along with the solvent 246 and impurities 220.

The following examples and test results are provided for the purposes of illustration and are not intended to limit the scope of the invention.

EXAMPLES

Example 1

The following example illustrates the effectiveness of one embodiment of the purification process of the present invention for obtaining purified cyclic esters of hydroxycarboxylic acids.

Cyclic Ester Production

A 5 g sample of racemic 2-hydroxyoctanoic acid, 0.22 g of Dowex-50 cation exchange resin in the acidic form (as a reaction catalyst), and 195 ml of toluene were added to a 3-neck flask fitted with a heating mantle, pot thermometer, magnetic stirrer, Dean-Stark tube, reflux condenser, and a rubber septum. The mixture was heated to reflux at a temperature of about 116° C. and held there for about 48 hours.

Aliquots of the reaction mixture were derivatized with diazomethane and analyzed by gas chromatography-mass spectrometry (GC-MS). Separate peaks were identified for: 2-hydroxyoctanoic acid, the linear ester formed from 2 molecules of 2-hydroxyoctanoic acid; the meso isomer of the cyclic diester of 2-hydroxyoctanoic acid; the D and L isomers of the cyclic ester of 2-hydroxyoctanoic acid; and a longer retention time peak for an unknown compound which was thought to be one or more higher linear esterification products.

Cyclic Ester Purification

A 300 ml sample of AMBERLYST® A-21 ion exchange resin was used as an adsorbent. The resin was first washed with several acetone rinses. The resin was placed in a 1 inch diameter column and then washed with a 1:1 mixture of toluene:acetone solution to displace any initial water held by the resin. The cyclic ester reaction mixture was diluted with acetone to a 1:1 toluene:acetone mixture and passed over the previously prepared AMBERLYST® A-21 ion exchange resin bed. The effluent was collected and evaporated to dryness. The solid product was analyzed by gas chromatography. Two peaks were found: the meso isomer of the cyclic diester of 2-hydroxyoctanoic acid, and the D and L isomers of the cyclic ester of 2-hydroxyoctanoic acid. Thus, purification of the cyclic ester was achieved in a non-stereospecific process, thereby allowing for recovery of a mixed isomeric population of cyclic esters which corresponds to the isomeric makeup of the feed to the adsorption process. The acid and linear esterification products of the hydroxycarboxylic acids were not found. A total of 0.6629 g of solid product was obtained giving an isolated yield of 34% of the theoretical yield calculated on a molar basis.

Example 2

The following example illustrates the production and purification of cyclic esters according to one embodiment of the present invention and subsequent production of polymers and also provides two comparative purification processes and attempts at polymerization.

Cyclic Ester Production

Crude tetramethyl glycolide was prepared by direct liquid phase synthesis from 2-hydroxy-2-methylpropionic acid using m-xylene as the solvent and p-toluene sulfonic acid as the catalyst. The mixture was refluxed using a Dean-Stark tube to remove water.

2.1 Cyclic Ester Purification and Polymerization

The crude tetramethyl glycolide was washed with sodium carbonate, neutralized, dried, and then dissolved in acetone. The crude teteramethyl glycolide/acetone solution was passed through a column containing AMBERLYST® A-21 ion exchange resin as an adsorbent to remove acid impurities. The column effluent was evaporated to dryness. The resulting solid was recrystallized using petroleum ether and dried. A sample of the resulting tetramethyl glycolide was analyzed by differential scanning calorimetry and was found to have a sharp melting point with onset at 80.9° C.

The purified tetramethyl glycolide was polymerized using lithium tert-butoxide catalyst for about 8 hours at about 130° C. The molecular weight of the resulting polymer was determined by gel permeation chromatography to have a $M_w$=520,000 and a $M_w$=354,000.

2.2 First Comparative Cyclic Ester Purification and Polymerization

The crude tetramethyl glycolide was washed with sodium carbonate, neutralized, and dried. The crude tetramethyl glycolide was dissolved and recrystallized using isopropanol as the solvent. A sample of the recrystallized material was analyzed by differential scanning calorimetry and was found to have a broad melting point with onset at 79.0° C.

A first attempt at polymerization of the purified material using stannous octoate as a catalyst failed. No detectable polymerization occurred and unreacted tetramethyl glycolide was recovered after a long reaction period.

A second attempt at polymerization of the purified material was partially successful. The polymerization was carried out at 130° C. using lithium tert-butoxide for the catalyst. The molecular weight of the resulting polymer was determined by gel permeation chromatography to have Mw=17, 200 and Mn=14,525. Only 42% of the starting monomer was converted to polymer.

The low molecular weights and poor conversions in this comparative example indicate that the solvent recrystallized tetramethyl glycolide was not of sufficient purity to produce high molecular weight polymer. In contrast, the adsorption based purification described in Example 2.1 was able to produce high purity tetramethyl glycolide suitable for producing high molecular weight polymer.

2.3 Second Comparative Cyclic Ester Purification and Polymerization

The crude tetramethyl glycolide was washed with sodium carbonate, neutralized, dried, then dissolved in acetone. The crude tetramethyl glycolide/acetone solution was passed through a resin bed containing AMBERLYST® A-21 ion exchange resin to remove any residual acid species. The column effluent was evaporated to dryness. The resulting solid was recrystallized from isopropanol and dried. A sample of the resulting tetramethyl glycolide was analyzed by differential scanning calorimetry and was found to have a sharp melting point with onset at 81.0° C.

An attempt at polymerizing the purified tetramethyl glycolide at 130° C. using lithium tert-butoxide catalyst failed. After eight hours, there was little evidence of polymerization. Residual traces of isopropanol in the purified tetramethyl glycolide are believed to have caused the failure of the polymerization. While drying of the purified tetramethyl glycolide removed the solvent adhering to the exterior of the crystals, it most likely did not remove the solvent trapped inside the occlusions of the crystals. It was, therefore, believed that there were trace levels of alcohol in the purified material.

The sharp melting point of this example indicates that the purity of the tetramethyl glycolide was comparable to the purity of the tetramethyl glycolide in Example 2.1 This example shows that even when an adsorption based process is followed by a positive purification step like solvent crystallization, that use of an alcohol solvent for crystallization introduced alcohol impurities into the cyclic ester composition which caused failure of polymerization.

Example 3

The following example illustrates the recovery of a mixed isomer lactide product to one embodiment of the purification and recovery process of the present invention.

Cyclic Ester Production

A 1025 g sample of mixed xylene, 50 μl of sulfuric acid, and some boiling chips were placed into a 2000 ml three neck flask fitted with a Dean-Stark tube, condenser, and heating mantle. The contents were heated to reflux and 50 ml of lactic acid solution was added. The lactic acid solution was made from 9 parts of 88% L-lactic acid and 1 part of 88% racemic lactic acid for an overall L:D ratio of 95:5 in the starting material. The reaction mixture was boiled at atmospheric pressure for about 4.5 hours during which time a total of 15 ml of water were collected in the Dean-Stark tube. The mixture was cooled to room temperature and allowed to phase split.

Cyclic Ester Purification

A 977 g sample of the upper phase material which contained lactide was added to a jar which contained 214 g of previously azeotropically distilled REILLEX® 425 ion exchange resin as an acid adsorbent, 144 g of 3A molecular sieves as a water adsorbent, and 50 g of activated carbon as an adsorbent for color bodies. This mixture was stirred for about 4 hours and a sample of the solution was taken and filtered through a 0.45 μm filter prior to analytical analysis.

High performance liquid chromatography (HPLC) analysis of the solution showed no detectable free acids. The lower detection limit of the HPLC method in this application was 2 meq free acid/kg of solution. The HPLC results also showed that the L:D:M isomer ratio of the material was unchanged by the adsorption treatments. Karl-Fisher titration showed that the treated solution contained 16.6 ppm of water.

Recovery of Mixed Isomer Lactide Product

The treated solution was then rotavaped to dryness to simulate the operations of a spray dryer. The cake residue was a white snow-like powder. Analysis of the cake showed that the L:D:M isomer ratio was 96.70:1.04:2.26, which indicates that a portion of the M-lactide was lost during the evaporation. This is not surprising given the higher vapor pressure of the M-lactide compared to the other isomers. A simple stripping section could be used to retain the M-lactide in industrial equipment. High performance liquid chromatography analysis of the powder showed no detectable free acids. The lower detection limit of the HPLC method in this application was 9 meq free acid/kg of lactide.

Example 4

The following example illustrates one embodiment of the regeneration processes for the adsorbents of the present invention.

An adsorption apparatus consisting of four 1" diameter insulated stainless steel tubes, each about 5 feet long, mounted vertically on a cart and connected in series. Sample ports were installed in the feed line, between each column, and in the effluent line. REILLEX® 425 resin was prepared to remove any water by azeotropic distillation with xylene. The four columns were filled with 311.6 g, 356.4 g, 370.1 g, and 352.3 g of wet resin, giving a total bed length of about 16 feet. Fresh xylene was pumped into the apparatus and air was bled from the system.

First Adsorption

A room temperature feed solution containing xylene, lactic acid, linear lactic acid esters, and lactide was pumped through the adsorption apparatus in an upflow direction at about 45 g/min, giving an upflow superficial velocity of 0.39 ft/min. Samples were taken every half hour at the five sample ports and submitted for high performance liquid chromatography (HPLC) analysis. After the initial xylene was displaced from the system, samples of the fourth column effluent showed no detectable levels of free acids until breakthrough of the column. Breakthrough of the fourth column occurred about 270 minutes after the feed solution was started. The lower detection limit of the HPLC method in this application was 2 meq free acid/kg of solution. An 807 g retain sample of the purified stream was taken from the fourth column prior to breakthrough. A 178 g sample of 3A molecular sieves was added to the retain sample. The retain sample was then stirred and stored for later use.

At about 270 minutes and beyond, the acid components broke through the fourth column in reverse molecular weight order. This observation indicates that the resin capacity decreases as the chain length of the linear lactic acid esters increases. The feed solution was stopped at about 480 minutes after it was started, at which time nearly complete saturation of the resin was observed.

Adsorbent Regeneration

The resin from the first column was removed and placed into a three neck flask fitted with a heating mantle and a condenser. Enough xylene was added to cover the resin, and the mixture was heated until boiling at about 133° C. After about a few minutes of boiling, the resin was filtered while hot. The resin was boiled in the same manner a second time in xylene, filtered, then placed back in the column. This thermal regeneration procedure was repeated for the second, third, and fourth columns. Fresh xylene was then pumped into the apparatus and air was bled from the system.

Second Adsorption

A second room temperature adsorption cycle was performed using the same xylene/lactic acid/lactide solution used in the first adsorption cycle. The flowrate for the second adsorption cycle was about 47 g/min, giving an upward superficial velocity of 0.41 ft/min. Samples were taken every half hour and submitted for HPLC analysis. After the initial xylene was displaced from the system, samples of the fourth column effluent showed no detectable levels of free acids until breakthrough of the column. Breakthrough of the fourth column occurred about 240 minutes after the start of the feed solution. As in the first adsorption cycle, the lower detection limit of the HPLC analysis in this application was 2 meq free acid/kg of solution. A 2580 g retain sample of the purified stream was taken from the fourth column prior to breakthrough. A 570 g sample of 3A molecular sieves were added to the retain sample. The retain sample was then stirred and stored for later use.

Since (1) the first adsorption cycle was carried out until near complete saturation of the resin, and (2) the length of the second adsorption cycle prior to breakthrough was about as long as the first adsorption cycle, the thermal regeneration of the resin was considered to have been substantially complete.

The two retain samples from first adsorption and second adsorption cycles were combined and a portion of the xylene was removed by rotavaping the material at 70° C. and partial vacuum. After rotavaping, the residue was cooled to room temperature during which time white needle-like crystals of L-lactide formed in the residue flask. The crystals were filtered, washed with fresh xylene which had been dried using 3A molecular sieves, then dried at 35° C. in a vacuum oven. The free acid level of the crystalline product was below the detection limit of a potassium methoxide titration method. The detection limit of the potassium methoxide titration method in this application was 0.02 meq free acid/kg of lactide.

Example 5

The following comparative example illustrates the high molecular weight of polymers which can be produced using the purified cyclic esters obtained according to one embodiment of the production and purification processes of the present invention relative to the molecular weight of polymers which can be obtained using commercially available cyclic esters.

Adsorbent Preparation

The first two tubes of the adsorption apparatus described in Example 4 were filled with REILLEX® 425. The REILLEX® 425 had been previously prepared by azeotropic distillation with xylene. The third and fourth tubes were filled with 3A molecular sieve beads. Xylene was pumped into the system, the molecular sieves allowed to degas, and the air purged from the columns.

Cyclic Ester Purification

A sample of 85 g of L-lactide were dissolved in 4 liters of xylene. The L-lactide was a commercial grade believed to be made from a depolymerization-based reaction. Prior to dissolution, the lactide was exposed to air for an extended period and allowed to pick-up water and form free acid. The starting lactide contained 91 meq free acid/kg lactide as determined by titration with potassium methoxide. Karl Fisher titration of the starting lactide, the starting xylene and lactide-xylene solution gave 260, 78 ppm and 84 ppm water, respectively.

The crude lactide-xylene solution was pumped through the adsorption apparatus at a rate of 46 g/min. After the initial xylene was displaced from the system, a 4 liter retain sample was taken from the fourth column effluent. High performance liquid chromatography (HPLC) analysis of the retain sample showed no detectable free acids. The lower detection limit of the HPLC method in this application was 2 meq free acid/kg solution. Karl Fisher titration of the retain sample showed 7.7 ppm of water.

Recovery of Cyclic Esters

A portion of the xylene from the retain sample was removed by rotavaping the material at 65° C. under partial vacuum. After rotavaping, the residue was cooled to room temperature during which time white needle-like crystals of L-lactide formed in the residue flask. The crystals were filtered, washed with fresh xylene which had been dried using 3A molecular sieves, then dried at 35° C. in a vacuum oven. The free acid level of the crystalline product was determined to be 0.04 meq free acid/kg lactide by potassium methoxide titration. Karl Fisher titration of the crystalline product showed 49 ppm of water.

Polymerization of Cyclic Esters

Six glass tubes were each filled with 10 grams of either the adsorption purified lactide, a commercial lactide, or the starting lactide material. The commercial lactide contained 1.1 meq free acid/kg lactide and 59 ppm water as determined by potassium methoxide titration and Karl Fisher titration. A 24 μl sample of a 10 wt % solution of stannous octoate in xylene solution was added to each tube, which corresponds to a catalyst level of 80 ppm molar or a 12500:1 monomer to catalyst ratio. The tubes were heated and the contents allowed to polymerize. The molecular weights shown below were determined by gel permeation chromatography analysis:

| Tube | Material | T (°C.) | t (hr) | Mw | Mn |
|---|---|---|---|---|---|
| 1 | Purified lactide | 167 | 4 | 399,800 | 255,325 |
| 2 | Commercial lactide | 167 | 4 | 268,700 | 130,135 |
| 3 | Starting lactide | 167 | 4 | 15,100 | 11,668 |
| 4 | Purified lactide | 145 | 44.5 | 441,100 | 179,600 |
| 5 | Commercial lactide | 145 | 44.5 | 196,400 | 94,200 |
| 6 | Starting lactide | 145 | 44.5 | 30,200 | 29,900 |

Since the molecular weights of the polymers derived from the purified lactide are about 2000% higher than those for the polymer derived from the starting lactide, the purification process was successful. The polymers from the purified lactide were 50–125% higher in molecular weight when compared to the polymers from the commercial lactide. Since the polymerization conditions were identical, the difference in molecular weights are due to differences in the monomer (lactide) purity.

Example 6

The following example illustrates another embodiment of the purification processes of the present invention.

Adsorbent Preparation

One hundred ml of dry AMBERLYST® A-21 resin was placed in a 1 inch diameter clean glass column. It was rinsed twice with 100 ml portions of acetone and once with 100 ml of 50 percent water/50 percent acetone. The first acetone rinse had a pH of 9 and was yellow, indicating impurities in the resin that were removed by this treatment. Magnesium sulfate (15 g) and 40 ml of 3A molecular sieves were added to the top of the column.

Adsorption of Impurities

A 10 g sample of L-lactide, 5 g of anhydrous lactic acid, 2 g polylactic acid and about 0.5 g distilled water were mixed with about 20 ml acetone and added to the column containing the adsorbents as prepared above. The lactide preparation was eluted from the column. The eluted fraction from the column was placed on a rotary evaporator while gently applying heat to remove the solvent. Residual acetone was further evaporated by placing the fraction in an oven over phosphorus pentoxide. A very white, light flaky material remained as a residue after the remaining acetone was driven off. The yield of lactide obtained was approximately 93.5%.

Example 7

The following example illustrates the improved shelf life and stability of a packaged cyclic ester product of the present invention.

One 5 kg sample of lactide is added to a 4 mil thick low density polyethylene (LDPE) bag having a water vapor transmission rate of about 0.39 g/(100 in$^2$·24 h) and another 5 kg sample of lactide is placed in a LDPE-foil laminate bag having a water vapor transmission rate of about 0.0006 g/(100 in$^2$·24 h). Both bags have 418 square inches of surface area. The bags of lactide are then stored at 100° F. and at 90% relative humidity for six months. The free acid level in the lactide in the 4 mil thick LDPE bag is measured and is found to have risen by 3332 meq free acid/kg lactide by the water transmitted through the LDPE bag. In contrast, the free acid level in the lactide in the LDPE-foil laminate bag is measured and is found to have risen by only about 5.4 meq free acid/kg lactide by transmitted water vapor.

Example 8

The following example illustrates the effectiveness of the aqueous solvent in removing lactic acid and its oligomers and water into a separate phase from the solvent and lactide.

A stream from the lactide reactor containing 1.139% by weight lactide and 0.728% by weight lactic acid and lactic acid oligomers with the remainder being xylene was contacted with 0.6% by weight water. The mixture was split into two separate phases, with one phase containing lactide and xylene and the other phase containing lactic acid, lactic acid oligomers, and water. The former phase was sampled and found to contain 1.127% by weight lactide and 0.05% by weight lactic acid and lactic acid oligomers and the latter phase 0.626% by weight lactide and 55.1% by weight lactic acid and lactic acid oligomers. Based on these concentrations and the relative volumes of the two phases, the former phase contained 99% of the lactide and 7% of the lactic acid and lactic acid oligomers.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the appended claims.

What is claimed is:

1. A process for the purification of cyclic esters in a composition comprising cyclic esters, an organic solvent and impurities, comprising:

introducing an aqueous solvent into said composition to form a mixture;

allowing said mixture to separate into a first phase comprising said cyclic esters and organic solvent and a second phase comprising said aqueous solvent and impurities, wherein the amount of aqueous solvent introduced into said composition is less than about 3% based on the weight of the composition above the mutual solubility limit of water in the organic solvent; and further purifying said cyclic ester in said first phase.

2. The process of claim 1, wherein said further purification is selected from the group consisting of adsorption, crystallization, distillation, and combinations thereof.

3. The process of claim 1, wherein said impurities removed by said second adsorbent comprise water.

4. A process for purification of cyclic esters in a composition comprising cyclic esters, an organic solvent and impurities, comprising:

(a) introducing an aqueous solvent into said composition and allowing said composition to separate into a first phase comprising said cyclic esters and organic solvent and a second phase comprising said aqueous solvent and impurities, wherein the amount of aqueous solvent introduced into said composition is less than about 3% by weight of the composition above the mutual solubility limit of water in the organic solvent; and (b) contacting said first phase with a first adsorbent to remove impurities.

5. The process of claim 4, wherein said impurities comprise free acid and said first adsorbent comprises an anion exchange resin.

6. The process of claim 4, further comprising the step of:

(c) contacting said first phase with a second adsorbent to remove impurities after said step of contacting with said first adsorbent.

7. The process of claim 6, wherein said impurities comprise water and said second adsorbent is selected from the group consisting of molecular sieves and alumina and silica gels.

8. The process of claim 6, wherein said composition before the introducing step comprises no more than about 1% by weight aqueous solvent.

9. The process of claim 6, wherein the amount of aqueous solvent introduced into said composition is less than about 3.0% by weight based on the weight of the composition above the mutual solubility limit of water in the organic solvent.

10. The process of claim 6, wherein the amount of said cyclic esters in said first phase is at least about 80% of the cyclic esters in said composition.

11. The process of claim 6, wherein at least about 60% by weight of said impurities in said composition separate into said second phase.

12. A process for the purification of cyclic esters in a composition comprising cyclic esters and impurities, wherein said impurities comprise XA composed of a compound selected from the group consisting of a hydroxycarboxylic acid, its ester, salt and amide ($X_1A$); a linear dimer molecule of $X_1A$ ($X_2A$); a linear trimer molecule of $X_1A$ ($X_3A$); a linear tetramer molecule of $X_1A$ ($X_4A$); a linear pentamer molecule of $X_1A$ ($X_5A$); and mixtures thereof, comprising:

introducing an aqueous solvent into said composition to form a mixture allowing said mixture to separate into a first phase comprising said cyclic esters and a second phase comprising said aqueous solvent and impurities, wherein the amount of aqueous solvent introduced into said composition is less than about 3% by weight of the composition above the mutual solubility limit of water in the organic solvent; and further purifying said cyclic ester in said first phase.

13. The process of claim 12, wherein said further purification is selected from the group consisting of adsorption, crystallization, distillation, and combinations thereof.

14. The process of claim 12, wherein said further purification comprises contacting said first phase with a first adsorbent to remove impurities.

15. The process of claim 14, wherein said further purification comprises contacting said first phase with a second adsorbent to remove impurities after said step of contacting with said first adsorbent.

16. The process of claim 15, wherein said impurities removed by said second adsorbent comprise water.

* * * * *